United States Patent [19]

Chang et al.

[11] Patent Number: 4,778,818

[45] Date of Patent: Oct. 18, 1988

[54] SUBSTITUTED 2-(HETEROARYL-2-PROPENYL)PHENOLS USEFUL AS ANTI-INFLAMMATORY AGENTS

[75] Inventors: Michael N. Chang, Westfield; Norman P. Jensen, Princeton; Milton L. Hammond, Somerville; Robert A. Zambias, Springfield, all of N.J.; John McDonald, Indianapolis, Ind.; Kathleen M. Rupprecht, Cranford, N.J.

[73] Assignee: Merck & Co., Inc., Rahway, N.J.

[21] Appl. No.: 39,407

[22] Filed: Apr. 17, 1987

Related U.S. Application Data

[62] Division of Ser. No. 764,446, Aug. 12, 1985, Pat. No. 4,686,235.

[51] Int. Cl.[4] ............... A61K 31/40; C07D 207/34

[52] U.S. Cl. .................. 514/423; 548/337; 548/343; 548/535; 548/543; 548/560; 548/251; 548/252; 548/253; 548/335; 549/51; 549/58; 549/78; 549/471; 549/475; 549/484; 549/491; 549/497; 549/501; 549/502; 514/277; 514/345; 514/381; 514/398; 514/399; 514/424; 514/427; 514/438; 514/443; 514/445; 514/448; 514/461; 514/469; 514/473; 546/298; 546/301; 546/326; 546/330; 546/344

[58] Field of Search ............... 546/298, 301, 326, 330, 546/344; 548/251, 252, 253, 335, 337, 343, 535, 543, 560; 549/51, 58, 471, 78, 475, 484, 491, 497, 501, 502; 514/277, 345, 381, 398, 399, 423, 424, 427, 438, 443, 445, 448, 461, 469, 473

[56] References Cited

PUBLICATIONS

Hurd et al., J.A.C.S., vol. 59, pp. 107–109 (1937).

*Primary Examiner*—Mary C. Lee
*Assistant Examiner*—Bernard I. Dentz
*Attorney, Agent, or Firm*—Theresa Y. Cheng; Michael C. Sudol; Mario A. Monaco

[57] ABSTRACT

Substituted cinnamyl-2,3-dihydrobenzofurans and analogs were prepared from the nucleophlic substitution of a cinnamylhalide with a 2,3-dihydrobenzofuran anion or an analog thereof. These compounds were found to be potent topical anti-inflammatory agents.

9 Claims, No Drawings

SUBSTITUTED 2-(HETEROARYL-2-PROPENYL)PHENOLS USEFUL AS ANTI-INFLAMMATORY AGENTS

This is a division of application Ser. No. 764,446, filed 8/12/85, now U.S. Pat. No. 4,686,235.

BACKGROUND OF THE INVENTION

The present invention relates to novel substituted cinnamyl-2,3-dihydrobenzofuran and analogs useful as anti-inflammatory agents useful as topical anti-inflammatory agents. A number of cinnamylphenols have been known to have antibiotic activities. For example, those disclosed in U.S. Pat. Nos. 3,745,222; 3,775,540; 3,777,037; 3,865,748; 3,936,393; 3,951,820; and 4,105,698. However, these patents did not disclose the novel compounds of the present invention especially those compounds related to substituted cinnamyl-2,3-dihydrobenzofurans or its analogs, nor did they disclose the newly discovered topical anti-inflammatory activity of these compounds.

We have found that the novel compounds are active in vitro in both the peritoneal macrophage assay and the polymorphonuclear leukocyte assay. We have also found these compounds are active in vivo in the topical mouse ear assay and the U.V. erythema assay for anti-inflammatory agents. However, these compounds tend to be inactivated in vivo and thereby are devoid of any significant systemic effects.

Recent studies demonstrated that macrophages participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteinases—the destructive peptide bond cleaving enzyme which has been shown to be directly involved in rheumatoid cartilage destruction; and (2) Prostaglandins (PG) (e.g., $E_2$ and $I_2$ by mouse peritoneal macrophages) and other arachidonic acid derivatives derived from both the cyclooxygenase and the lipoxygenase pathways.

These archidonic acid oxygenation products have been identified as the critical mediators of various inflammatory conditions.

Interruption of these pathways by enzyme inhibition has been explored for effective therapy. For example, non-steroidal anti-inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, Science, 220, 568 (1983); D. Bailey et al, Ann. Rpts. Med. Chem., 17, 203 (1982)).

Conditions involving elevated intraocular pressures which are too high for normal function may result in irreversible loss of visual function. For example, glaucoma, if untreated, may lead to ocular hypertension, inflammation, and eventually blindness.

To be an effective and acceptable topical agent, for treating inflammation in the eye, such as that caused by glaucoma or other eye diseases, the drug must not only penetrate the ophthalmic tissues to reach the active sites within the eye, but it must also be devoid of those side effects including irritation, allergic reaction and the like which would militate against long term administration.

Accordingly, pharmacological agents which are capable of inhibiting the formation of, the release of a mediator from, or the function of macrophages or polymorphonuclear leukocytes may also be effective agents in the treatment of various inflammatory conditions, e.g., pain, fever, rheumatoid arthritis, osteoarthritis, bronchial inflammation, inflammatory bowel disease, asthema, allergic disorders, skin diseases, cardiovascular disorders, glaucoma, emphysema, acute respiratory distress syndrome, spondylitis, lupus, gout, psoriasis, and other prostaglandins and/or leukotriene mediated diseases.

Regarding the topical mouse ear assay, it has been previously established that classical nonsteroidal anti-inflammatory agents such as indomethacin and steroidal anti-inflammatory agents such as dexamethsone are active in this assay.

With respect to the U.V. erythema assay, it has been shown previously that the U.V. erythema condition is partially the result of a local release of prostaglandins derived oxidatively from arachiodonic acid by the action of PG synthetases, e.g., cyclooxygenase. Therefore, pharmacological agents which inhibit the erythema are generally considered to be active topical anti-inflammatory agents.

Furthermore, anti-inflammatory agents which are not significantly systemically active are advantageous in the sense that they are not subject to the adverse effects, e.g., gastrointestinal ulcerations and bleeding that often plagued users of systemic NSAIDs (non-steroidal anti-inflammatory agents). Accordingly, an object of this invention is to provide novel substituted cinnamyl-2,3-dihydrobenzofuran derivatives and analogs as dual enzyme inhibitors of cyclooxygenase and lipoxygenase and particularly as topical anti-inflammatory agents. These agents are especially useful in the treatment of, among others, dermal inflammatory conditions and prusitus such as sunburn, erythema, eczema, contact dermatitis, allergic dermatitis, eye inflammation caused by glaucoma, and psoriasis. They are also useful for topical application to prevent periodontal diseases.

Another object of this invention is to provide appropriate processes for the preparation of the subject novel compounds.

Still a further object of the present invention is to provide a pharmaceutically acceptable composition containing an effective amount of the active compound for the treatment of various dermatological inflammatory conditions.

Finally, it is the ultimate object of this invention to develop a method of treating dermal inflammation via the administration of a therapeutically effective amount of the novel compounds or pharmaceutically acceptable compositions thereof to a mammalian species in need of such treatment.

DETAILED DESCRIPTION OF THE INVENTION

A. Scope of the Invention

This invention relates to novel compounds of formula (I) and the corresponding open-chain analogs of formula (II):

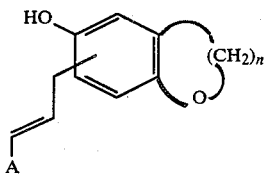

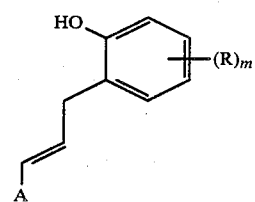

or a pharmaceutically acceptable salt thereof.
Wherein
R is
  (a) hydroxyloweralkyl;
  (b) lower alkanoyl;
  (c) CN;
  (d) halo;
  (e) mercaptoloweralkyl especially mercapto $C_{1-6}$alkyl such as —$CH_2SR^2$ where $R^2$ represents H or loweralkyl,
  (f) loweralkylthio especially $C_{1-6}$alkylthio such as —$SCH_3$;
  (g) lowerhaloalkyl;
  (h) —$COOR^2$;
  (i) hydroxycarbonylloweralkyl especially hydroxycarbonyl-$C_{1-6}$alkyl such as —$CH_2COOH$;
  (j) loweralkoxycarbonylloweralkyl especially $C_{1-6}$alkoxycarbonyl $C_{1-6}$alkyl such as —$CH_2COO$ t-Bu;
  (k) haloloweralkanoyl especially halo $C_{1-6}$ alkanoyl such as trifluoroacetyl;
m is 1 to 4;
n is 2 or 3;
A is
  (a) phenyl substituted with $(R^1)_q$ wherein when there are more than one $R^1$ (q 1) $R^1$ can be the same or different from each other and is
    (1) hydrogen;
    (2) halo especially fluoro, chloro or bromo;
    (3) loweralkoxy especially $C_{1-6}$ alkoxy, e.g., methoxy, ethoxy, isopropoxy, t-butoxy or cyclohexyloxy, or —$OCH_2O$—;
    (4) lower alkylthio especially $C_{1-6}$alkylthio, or $C_{1-6}$haloalkylthio e.g., methylthio, ethylthio, trifluoromethylthio or cyclohexylthio;
    (5) lower alkyl sulfinyl especially $C_{1-6}$alkyl sulfinyl, e.g., methyl sulfinyl, i-propyl sulfinyl, and cyclopentyl sulfinyl;
    (6) lower alkyl sulfonyl especially $C_{1-6}$alkyl sulfonyl such as methyl sulfonyl, ethyl sulfonyl and n-butyl sulfonyl;
    (7) unsubstituted or substituted phenyl loweralkoxy such as benzyloxy;
    (8) loweralkyl especially $C_{1-6}$alkyl such as methyl, ethyl, propyl, t-butyl, pentyl, benzyl, cyclopropyl, cyclopentyl or cyclohexyl;
    (9) loweralkenyl especially $C_{2-6}$alkenyl, for example, vinyl, allyl, and buten-2-yl;
    (10) lower alkanoyl especially $C_{1-6}$alkanoyl such as formyl, acetyl or i-propanoyl;
    (11) haloloweralkyl especially $C_{1-6}$haloalkyl such as trifluoromethyl;
    (12) —COOH;
    (13) aryl especially phenyl or substituted phenyl, e.g., 4-methoxyphenyl, 2,4-difluorophenyl or 3-chlorophenyl; or
    (14) aryloxy especially phenoxy;
    (15) cyano;
    (16) hydroxyloweralkyl especially hydroxy $C_{1-3}$alkyl such as —$CH_2OH$;
    (17) halo loweralkanoyl especially halo$C_{1-6}$alkanoyl eq. $CF_3CO$;
    (18) heteroaryl as defined below; or
    (19) loweralkanoyloxy especially acetyloxy;
  q is 0 to 5;
  (b) unsubstituted or substituted heteroaryl, for example:
    (1) thienyl;
    (2) benzothienyl;
    (3) furyl;
    (4) benzofuryl;
    (5) pyrryl;
    (6) indolyl;
    (7) thiazolyl;
    (8) benzothiazolyl;
    (9) thiadiazolyl;
    (10) benzothiadiazolyl;
    (11) quinolyl;
    (12) isoquinolyl;
    (13) pyridyl;
    (14) pyrazinyl;
    (15) tetrazolyl;
    (16) triazolyl; or
    (17) imidazole;

the heteroaryl above can be substituted with one or more of $R^1$, e.g., $C_{1-6}$alkyl, $C_{1-6}$alkanoyl, $C_{1-6}$haloalkyl, halo, cyano, cyano, or hydroxy $C_{1-3}$alkyl.

In a preferred embodiment of this invention, the compounds are of formula (II)
wherein
R is
  (a) $COOR^2$;
  (b) loweralkoxy;
  (c) haloloweralkylcarbonyl especially halo$C_{1-6}$alkylcarbonyl such as $CF_3CO$—;
  (d) halo;
  (e) loweralkanoyl especially acetyl;
  (f) lowerhaloalkyl especially trifluoromethyl;
  (g) hydroxyloweralkyl eg. —$CH_2OH$; or
  (h) cyano;
A is phenyl substituted with $(R^1)_q$ where $R^1$ and q are as previously described; and
m is 1 to 3.

In a more preferred embodiment of this invention, the compounds are of formula (I)
wherein
A is phenyl substituted with $(R^1)_q$ wherein $R^1$ is
  (a) hydrogen;
  (b) loweralkoxy;
  (c) halo;
  (d) lowerhaloalkyl, (e) loweralkanoyl;
(f) hydroxyloweralkyl; or
(q) CN;
q is 1 or 2; and
n is 2 or 3.

In the even more preferred embodiment of the present invention, the compounds are of the following formulae:

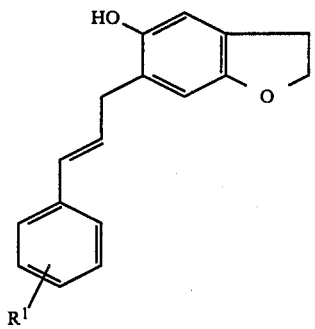
(a)

and

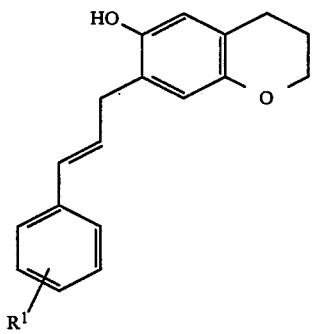
(b)

wherein $R^1$ is loweralkanoyl or hydroxyloweralkyl.

B. Preparation of the Compounds within the Scope of the Invention

The novel compounds of the present invention are prepared from the following processes:

Scheme (a)

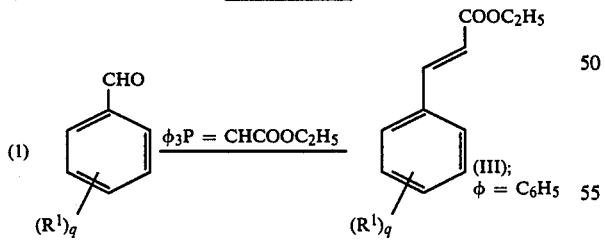

(2) (III) $\xrightarrow{\text{Reduction}}$

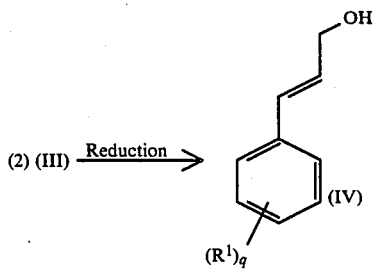

-continued
Scheme (a)

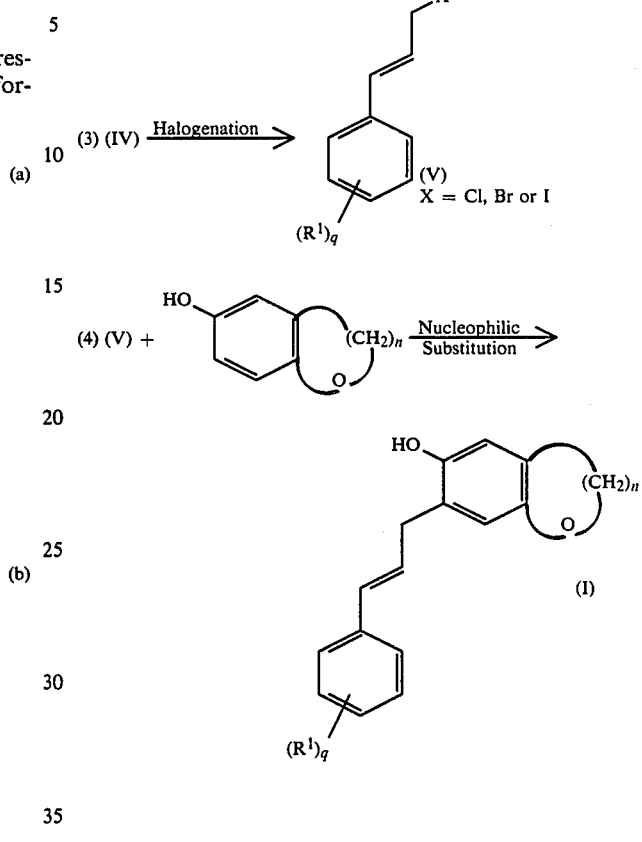

Scheme (b)

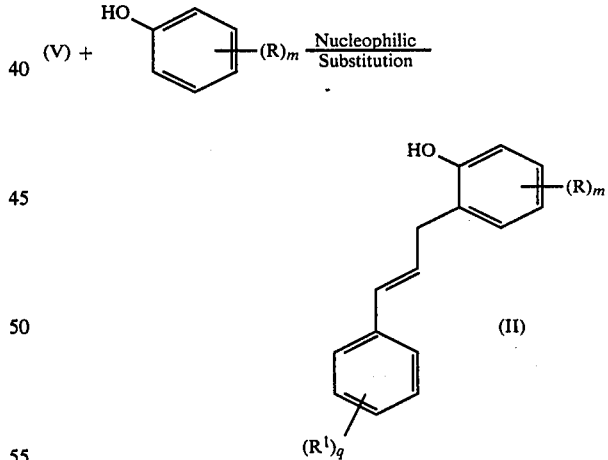

Scheme (c)

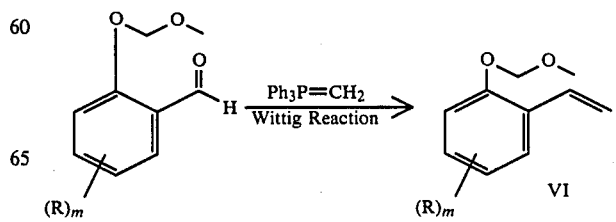

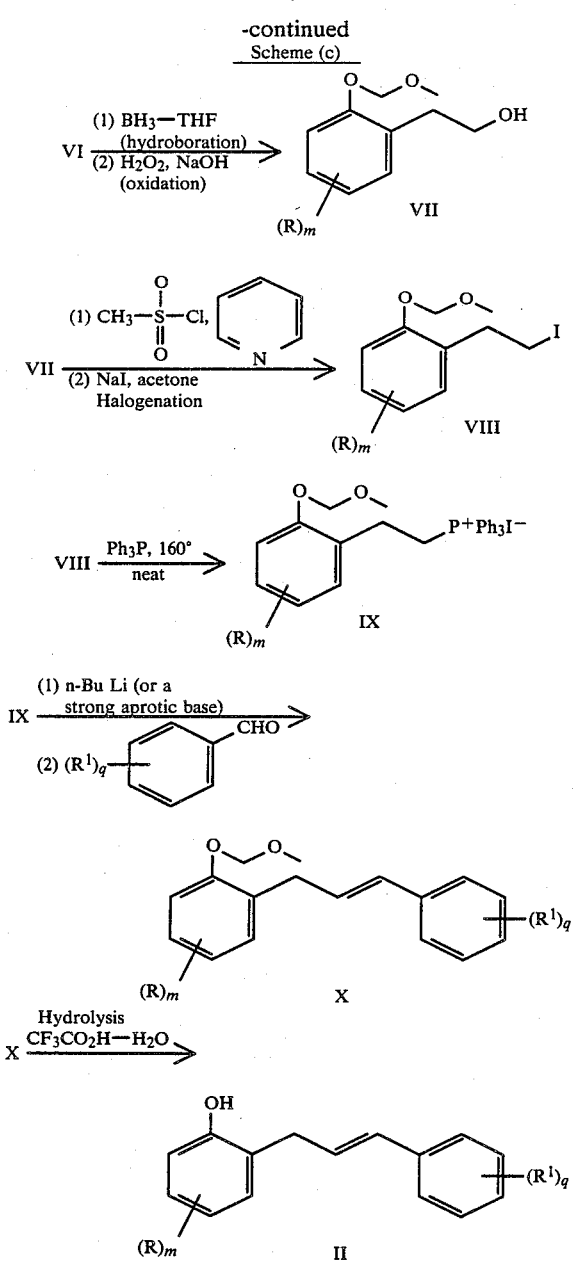

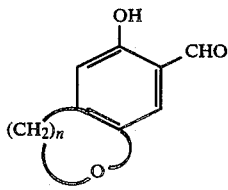

Scheme (c) is applicable to the preparation of a compound of formula I from the aldehyde of formula The procedures of the above synthetic schemes (a) and (b) are known for the preparation of cinnamylphenols of formula (II), i.e., those disclosed in U.S. Pat. Nos. 3,745,222; 3,775,540; 3,777,039; 3,865,748; 3,936,393; 3,951,820; and 4,105,698. However, these procedures have not been applied to prepare the cinnamyl-2,3-dihydrobenzofuran derivatives of formula (I).

The alkylations described in Schemes (a) and (b) are useful only when the cinnamyl bromide (V) is unsubstituted or substituted with electron-withdrawing groups. Analogs with electron-donating substituents or with electron-rich heterocycles must be prepared by Scheme (c). Any analogs that are prepared by Schemes (a) and (b) may be synthesized according to Scheme (c) by using the appropriate Wittig reagent (IX). This includes cinnamyl-2,3-dihydrobenzofurans which would utilize the Wittig reagent XI

C. Utility of the Subject Compounds of the Invention

This invention also relates to a method of treating topical inflammation in patients in need of such treatment. Generally, a sufficient amount of a compound of formulae (I) or (II) or a pharmaceutical composition thereof, particularly an especially preferred compound, is administered to the patient as the active constituent.

The topical mouse ear assay (TME) was used to evaluate the novel compounds of the present invention for its effect on inflammatory responses elicited by topically applied phorbol myristate acetate (PMA) or topically applied archidonic acid (AA). The inflammatory responses may be in the form of edema (measured by net weight); vascular permeability (measured by $^{125}$I-BSA accumulation); of PMN infiltration (measured by myeloperoxidase activity). A protocol of the assay and some results derived therefrom are summarized in Table I.

TABLE I Topical Mouse Ear Assay

Method: The right ears of mice (5 mice per group) were treated topically with either 5 μl PMA or 1000 μg AA alone or with the test compound in 25 μl of vehicle. The vehicle was water/pyridine/acetone (1:2:97). A control group of mice received the vehicle only. The mice were allowed food and water ad libitum during the treatment period; 2 hours for AA and 4 hours for PMA. The mice were sacrificed by cervical dislocation and a 6 mm diameter disc of tissue punched from both the treated and untreated ears. The tissue biopsies were immediately weighed and the weight increase of the treated ear relative to the weight of the untreated ear determined.

For the determination of vascular permeability, 1 μM $^{125}$I-bovine serum albumin ($^{125}$I-BSA) was administered in 0.5 ml phosphate buffered saline 15 min prior to the topical application. At the termination of the experiment, the amount of radioactivity in both the treated and untreated ear biopsies was determined and the increased amount of radioactivity in the treated tissue relative to the amount of radioactive in the untreated tissue determined.

As a measure of PMN infiltration, the amount of myeloperoxidase (MPO) activity in the same tissues was determined. The tissue biopsies were homogenized into 1 ml 0.5% hexadecyltrimethylammonium bromide and centrifuged for 45 min. at 1200×g. Aliquots 40 μl, of the supernatant phases were assayed for MPO activity by a colorimetric method devised by H. Dougherty for automated Titertek analysis. The MPO activity is expressed as the $OD_{450}$ of the treated ear homogenate minus the $OD_{450}$ of the non-treated ear homogenate.

All of the data are expressed as the mean±SEM, N=5 mice/group.

Results: The effect of 5-hydroxy-6-(2-hydroxymethylcinnamyl)-2,3-dihydrobenzofuran (A)

| Compound | Dosage (μg) | Edema (% inhibition) |
|---|---|---|
| A | 300 | 88 |
|  | 150 | 54 |
|  | 50 | 37 |
| Indomethacin | 150 | 51 |
| Dexamethasone | 5 | 60 |

For the treatment of inflammation, arthritis conditions, cardiovascular disorder, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques.

Particularly, the pharmaceutical compositions containing the active ingredient may be in a form suitable for topical use, for example, aqueous or oily solutions or suspensions, dispersible powders or granules, tinctures, topical aerosol emulsions, creams, ointments, jellies, suppositories or the like. Compositions intended for topical use may be prepared according to any method known to the art for the manufacture of pharmaceutical compositions and such compositions may contain one or more active compounds.

Aqueous suspensions contain the active materials together with excipients suitable for the manufacture of aqueous suspensions. Such excipients are suspended agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soy bean lecithin, and esters or partial esters derived from fatty acids and hexitol anhydrides, for example, sorbitan mono-oleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl caproate and ethyl laurate. Suitable glycols include propylene glycol, butylene glycol, polyethylene glycol and the like. Generally, a caboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated conditions (10 mg to 7 gms per patient per day). For example, inflammation may be effectively treated by the administration from about 0.5 to 50 mg of the compound per kilogram of body weight per day (25 mg to 5 gms per patient per day). Advantageously, from about 2 mg to about 20 mg per kilogram of body weight per daily dosage produces highly effective results (50 mg to 1 gm per patient per day).

Particularly, for use in treatment of ophthalmic conditions including eye inflammation caused by glaucoma or other eye diseases, the active compound can be administered topically or systemically when it is appropriate. The dose administered can be from as little as 0.1 to 25 mg or more per day, singly, or preferably on a 2 to 4 dose per day regimen although a single dose per day is satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling inflammation. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The amount of active ingredient that may be combined with the carrier materials to produce a single dosage form will vary depending upon the host treated and the particular mode of administration. Dosage unit forms will generally contain between from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Set forth below are some illustrative topical formulations containing a selected active compound of the instant invention.

FORMULATION 1-SOLUTION (a) Distilled water qs to 100%
Procedure: Dissolve compound (A) in enough water to make 100%. Filter the solution. Apply to the affected area.

FORMULATION 2-TINCTURE (b) Alcohol U.S.P.—50%
Water qs to 100%
Procedure: Dissolve compound (A) in the alcohol. Add sufficient water to make 100%. Filter and apply to affected area.

FORMULATION 3-TOPICAL AEROSOL (c) Alcohol U.S.P.—5%
Isopropylmyristate—5%
Conventional halogenated hydrocarbon propellant qs 100% e.g., Freon 11 (trichlorofuluromethane), Freon 12 (dichlorodifluoromethane), Freon 14 (carbon tetrafluoride), Freon C 318 (Octafluorocyclobutane), Freon 114 (Cryofluorane), etc.
Procedure: Dissolve Compound (A) in the alcohol and isopropylmyristate. Add sufficient halogenated propellant and introduce into conventional aerosol containers either by pressure or by cold filing. Apply to affected area.

FORMULATION 4-OINTMENT

Petrolatum U.S.P. qs to—100%
Procedure: Heat the petrolatum to 60° C. Add compound (A) and stir until thoroughly dispersed. Cool to room temperature. Apply to affected area.

FORMULATION 5

| A Compound of formula (I) | 1 mg. | 15 mg. |
| --- | --- | --- |
| Monobasic sodium phosphate.2H$_2$O | 10 mg. | 5 mg. |
| Dibasic sodium phosphate.12H$_2$O | 30 mg. | 15 mg. |
| Benzalkonium chloride | 0.1 mg. | 0.1 mg. |
| Water for injection q.s. ad. | 1.0 ml. | 1.0 ml. |

A compound of formula (I), phosphate buffer salts, and benzalkonium chloride are added to and dissolved in water. The pH of the composition is adjusted to 6.8 and diluted to volume. The composition is rendered sterile by ionizing radiation.

FORMULATION 6

| A Compound of formula (I) | 5 mg. |
| --- | --- |
| petrolatum q.s. ad. | 1 gram |

The active compound and the petrolatum are aseptically combined.

FORMULATION 7

| A Compound of formula (I) | 1 mg. |
| --- | --- |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

FORMULATION 8

| A Compound of formula (I) | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

FORMULATION 9

| A Compound of formula (I) | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

FORMULATION 10

| A Compound of formula (I) | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

FORMULATION 11

The following materials are admixed in a 1250 ml bottle: 24 g of an active compound, e.g., 5-hydroxy-6-(2-hydroxymethylcinnamyl)-2,3-dihydrobenzofuran, which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psig. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock solutions are then prepared for polyoxyethylene (20) sorbitan monooleate by dissolving 3 g of the material in 100 ml of water, and of benzyl alcohol/$\beta$-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

FORMULATION 12

Solution Composition

| 5-hydroxy-6-(2-hydroxymethyl-cinnamyl)-2,3-dihydrobenzofuran | 0.1 mg. |
|---|---|
| Peanut oil q.s. ad. | 0.11 mg. |

The solution is rendered sterile by filtration through a sterilizing filter.

FORMULATION 13

| A compound of formula (I) | 0.5 gm. |
|---|---|
| Petrolatum q.s. ad. | 1 gram |

The compound and the petroleum are aseptically combined.

EXAMPLE 1

6-cinnamyl-2,3-dihydro-5-hydroxybenzofuran

Sodium hydride (0.40 g; 10 mM; 60% in mineral oil) was washed twice with hexane under nitrogen. The sodium hydride was suspended in 15 ml of benzene and 5-hydroxy-2,3-dihydrobenzofuran (1.00 g; 7.37 mM) was added in 20 ml of benzene in one portion. The suspension was stirred at room temperature for 1.5 hours giving a pale blue suspension. Cinnamyl bromide (freshly distilled; b.p.=76°-8° at 0.2 torr; 1.58 g; 8.0 mM) was added in 15 ml of benzene. The reaction was then heated to reflux for 3.5 hours. After cooling the reaction mixture was poured into 1N aqueous hydrochloric acid, partitioned and back extracted with ether. The combined organic layers were dried over magnesium sulfate, filtered, and stripped to a brown oil. The crude reaction product was flash chromatographed with 600 ml of 20% ethyl acetate in hexane on a 30 mm by 6" column of silica gel. This chromatography gave a mixture of product and starting phenol which were separated by chromatography on one cartridge in the Waters Prep 500 with 2 gallons of 20% ethyl acetate in hexane and four recycles with peak having techniques. The resulting semipurified product was crystallized from benzene/hexane to 0.516 g (28% yield). of 6-cinnamyl-2,3-dihydro-5-hydroxybenzofuran.

NMR (CDCl$_3$): δ 7.0–7.3 (m; 4H); 6.16–6.62 (m; 4H); 4.43 (s; 1H); 4.40 (t (8 Hz); 2H); 3.40 (d(5 Hz); 2H); 3.03 (t(8 Hz); 2H).

IR: 3700, 2920, 1610, 1490, 1425, 1140, 981, 870 cm$^{-1}$ (CHCl$_3$).

MS: 252 (M+) (68%); 161 (34%); 148 (100%); 91 (36%).

| Microanalysis: | C | H |
|---|---|---|
| Calculated: | 80.92 | 6.39 |
| Found: | 80.50 | 6.05 | m.p.=85°–87° C.

EXAMPLE 2

6-(o-Bromocinnamyl)-2,3-dihydro-5-hydrobenzofuran

Step A: Preparation of o-bromocinnamylalcohol

Ethyl o-bromocinnamate (66.3 g; 260 mM) was dissolved in 750 ml of anhydrous toluene under nitrogen in a three-neck round bottom flask equipped with addition funnel and condensor. A toluene solution of diisobutylaluminum hydride (520 mM; 1.53M) was transferred via canula to the addition funnel and then added dropwise to the reaction mixture, which had been chilled to −78°. After the addition was completed the reaction was warmed to ambient temperature over a 1.5 hour period and quenched by the dropwise addition of 50 ml of water. Some cooling was required. The resulting emulsion was added to 640 ml of 2N aqueous hydrochloric acid. After partitioning the slightly acidic (pH 5) aqueous layer was extracted twice with ether. The combined organic fractions were dried (MgSO$_4$), filtered (fritted funnel), and evaporated to afford an oil. The oil was chromatographed in two portions on the Waters Prep 500 equipped with two cartridges eluting with a total of two gallons of 35% ethyl acetate in hexane. This produced 33.8 g (61% yield) of o-bromocinnamylalcohol. NMR (CDCl$_3$): δ 6.8–7.8 (m; 5H); 6.0–6.6 (AB; 1H); 4.2–4.4 (brd.; 2H); 2–2.6 (brs; 1H).

Step B: Preparation of o-bromocinnamylbromide

All of the o-bromocinnamylalcohol (159 mM) from Step A was dissolved in 300 ml of carbon tetrachloride under nitrogen and chilled to 0°. Then 100 ml of carbon tetrachloride containing phosphorous tribromide (5.62 ml; 59.8 mM) was added dropwise. After stirring at 0° for an additional hour the reaction was poured into ice water and partitioned. The aqueous layer was extracted once with methylene chloride and the combined organic layers were washed with cold 1.5N aqueous sodium hydroxide. Drying over magnesium sulfate followed by solvent removal gave a pale yellow oil, which was purified by short path distillation at 0.2 torr. The o-bromocinnamyl bromide was distilled at 105° and 37.3 g (85% yield) was isolated. NMR (CDCl$_3$): δ 6.8–7.7 (m; 5H); 6.33 (AB; 1H); 4.15 (d; 2H).

Step C: Preparation of 6-(o-bromocinnamyl)-2,3-dihydro-5-hydroxybenzofuran

Sodium hydride (0.72 g; 18 mM, 60% in mineral oil) was washed twice with hexane under a stream of nitrogen. It was then suspended in 25 ml of anhydrous benzene in a 250 ml side-arm round bottom flask equipped with a dropping funnel. The 5-hydroxy-2,3-dihydrobenzofuran was added in one portion (1.63 g; 12.0 mM) i 40 ml of benzene under positive nitrogen pressure and the resulting suspension was stirred at room temperature for 45 minutes. o-Bromocinnamyl bromide was then added in 15 ml of benzene. No reaction was observed at R.T. or at 50° so the reaction was heated to 75° for two hours at which time the reaction was cooled to 23° and poured into dilute hydrochloric acid solution. This was extracted 3 times with ether, dried over magnesium sulfate, and stripped to a brown oil. This crude material was purified by chromatography on a Waters' Prep 500 equipped with one cartridge and eluted and recycled with 20% ethyl acetate in hexane. Recrystallization from ethyl acetate/hexane gave 1.58 g (40%) of tan crystals identified spectrally as 6-(o-bromocinnamyl)-2,3-dihydro-5-hydroxybenzofuran.

NMR (CDCl$_3$): δ6.6–7.4 (m; 4H); 6.4–6.6 (m; 3H); 6.08 (dqt (16 Hz and 6 Hz); 1H); 4.67 (s; 1H); 4.40 (t(8 Hz); 2H); 3.43 (d(6 Hz); 2H); 3.03 (t(8 Hz); 2H).

IR: 3700, 3500, 2950, 1480, 1430, 1330, 1280, 1160, 1140, 1020, 980, 965, 945, 865 cm$^{-1}$ (CHCl$_3$).

| Microanalysis: | C | H | Br |
|---|---|---|---|
| Calculated: | 61.65 | 4.57 | 24.13 |
| Found: | 61.73 | 4.53 | 23.88 |

EXAMPLE 3

6-(o-cyanocinnamyl)-2,3-dihydro-5-hydroxy-benzofuran 6-(o-Bromocinnamyl)-2,3-dihydro-5-hydroxybenzofuran (1.49 g; 4.5 mM) and cuprous cyanide (1.37 g; 15.3 mM) were suspended in 18 ml of anhydrous N-methyl-2-pyrrolidinone. Nitrogen was bubbled through this suspension for approximately 15 minutes and the reaction mixture was then heated to 175° under nitrogen for 2 hours. After cooling to ambient temperature the reaction was poured into 60 ml of water containing 60 ml of concentrated ammonium hydroxide. This emulsion was extracted three times with ether, dried over magnesium sulfate and stripped to a brown oil. Flash chromatography of this material on a 30 mm by 5½" column of silica gel eluted with 500 ml of 35% ethyl acetate in hexane gave a solid which was recrystallized from ethyl acetate/hexane producing 0.95 g (76%) of white crystals identified as 6-(o-cyanocinnamyl)-2,3-dihydro-5-hydroxy-benzofuran.

NMR (CDCl$_3$): δ 7.2–7.6 (m; 4H); 6.2–6.8 (m; 4H); 4.60 (s; 1H); 4.43 (t(9 Hz); 2H); 3.50 (d(6 Hz); 2H); 3.07 (t(9 Hz); 2H).

IR: 3700, 3450, 2900, 2250, 1600, 1470, 1420, 1150, 1140, 980, 960, 940, 900, 860 cm$^{-1}$.

| Microanalysis: | C | H | N |
|---|---|---|---|
| Calculated: | 77.96 | 5.45 | 5.05 |

| Microanalysis: | C | H | N |
|---|---|---|---|
| Found: | 77.67 | 5.28 | 4.83 | m.p.=137°-9°.

EXAMPLE 4

2,3-dihydro-5-hydroxy-6-(o-hydroxymethylcinnamyl)-benzofuran

A round bottom flask, equipped with a dropping funnel, was flame-dried under nitrogen and charged with 23 ml of anhydrous benzene and 6-(o-cyanocinnamyl)-2,3-dihydro-5-hydroxybenzofuran (0.85 g; 3.1 mM). This solution was chilled in an ice bath and 4.5 ml (6.9 mM) of diisobutylaluminum hydride in toluene was added dropwise. The reaction was stirred at 0° for one hour and then poured into 1N aqueous hydrochloric acid. This resulted in an emulsion which was filtered through celite and partitioned. The aqueous phase was extracted with ether and the combined organic layers were dried over magnesium sulfate. The suspension was filtered and stripped of solvent in vacuo. The resultant brown solid was taken up in 75 ml of methanol and sodium borohydride (170 mgs) was added in portions with the usual gas evolution. The reaction was stirred at room temperature for 30 minutes and the solvent was then removed at reduced pressure. The resulting oil was purified by flash chromatography on a 30 mm by 5½" column of silica gel eluted with 600 ml of 30% ethyl acetate in hexane. This gave only 106 mg (13%) of 2,3-dihydro-5-hydroxy-6-(o-hydroxymethylcinnamyl)-benzofuran.

NMR (CDCl$_3$): δ8.17 (s; 1H); 6.9-7.3 (m; 4H); 6.64 (d(15 Hz); 1H); 6.63 (s; 1H); (CDCl$_3$/DMSO-D$_6$) 6.33 (s; 1H); 6.13 (d of t (15 Hz and 7 Hz); 1H); 4.42 (s; 2H); 4.36 (t(8 Hz); 2H); 3.40 (d(7 Hz); 2H); 3.03 (t(8 Hz); 2H); 2.98 (s; 1H).

EXAMPLE 5

5-cinnamyl-2,3-dihydro-6-hydroxybenzopyran

Step A: Preparation of p-propargyloxyphenol

Hydroquinone (49.6 g; 450 mM) was dissolved in 700 ml of anhydrous acetone in a two liter, 3-necked, round bottom flask equipped with reflux condensor, air stirrer and nitrogen bubbler. Potassium carbonate (65.6 g; 460 mM) was ground finely and then added to the reaction followed by propargylbromide (53.6 g; 450 mM). The reaction was heated at reflux for three days, cooled to room temperature, filtered and the solvent removed. The residue was taken up in ether and extracted three times with 2.5N aqueous sodium hydroxide. The basic layers were acidified with concentrated hydrochloric acid while adding ice and extracted twice with ether. The combined ethereal layers were dried over magnesium sulfate, charcoal was added, and the mixture was filtered through celite. The solvent was removed in vacuo and the remaining dark brown sludge was purified by chromatography in two portions on a Waters Prep 500 equipped with two silica gel cartridges and eluted with 20% ethyl acetate in hexane after injecting in ether solution. This produced 21.4 g (64% of theory) of the desired p-propargyloxyphenol.

NMR (CDCl$_3$): δ 6.5-6.8 (m; 4H); 5.53 (s; 1H); 4.50 (d(2 Hz); 2H); 2.40 (t(2 Hz); 1H).

Step B: Preparation of 6-hydroxybenzopyran

Nitrogen was bubbled through 100 ml of diethylaniline for 15 minutes and 5.0 g (34 mM) of p-propargyloxyphenol was added in one portion. The reaction mixture was heated to 200° under nitrogen overnight. The brown solution was poured into 600 ml of ether and extracted twice with 2.5N aqueous sodium hydroxide. The combined aqueous layers were extracted once with ether and then acidified with concentrated hydrochloric acid at 0°. The acidic phase was extracted twice with ether. The ether extracts were dried over magnesium sulfate, decolorized with charcoal, and filtered through celite. Solvent removal in vacuo gave a reddish-brown oil which was purified by flash chromatography on a 30 mm by 5½" column of silica gel eluted with 600 ml of 20% ethyl acetate in hexane. This produced 2.96 g (59%) of 6-hydroxybenzopyran as a yellow oil.

NMR (CDCl$_3$): δ 6.0-6.8 (m; 4H); 5.5-5.8 (do(t(11 Hz and 4 Hz); 1H); 5.45 (s; 1H); 4.63 (d of t(4 Hz and 2 Hz); 1H).

IR: 3750, 3450, 2900, 1640, 1580, 1490, 1450, 1370, 1280, 1160, 1140, 1110, 1030, 1015, 942, 920, 840, 830 cm$^{-1}$.

Step C: Preparation of 2,3-dihydro-6-hydroxybenzopyran

The 6-hydroxybenzopyran (1.5 g; 10 mM) was dissolved in 100 ml of anhydrous benzene along with Wilkinson's catalyst (280 mgs; 0.30 mM). This hydrogenation bottle containing this reaction mixture was first flushed with nitrogen and then with hydrogen. The bottle was pressurized to 40 psi in a Parr shaker and agitated for 40 minutes at which time the pressure in the bottle (400 ml dead volume) had dropeed to 30 psi and was dropping no further. The bottle was then flushed with nitrogen and the solvent was removed in vacuo. The residue was taken up in ether and filtered through a pad of celite. The solvent was removed and the oil was purified by flash chromtography on a 30 mm×6" column of silica gel eluted with 600 ml of 20% ethyl acetate in hexane. This purification produced 1.40 g (93%) of 2,3-dihydro-6-hydroxybenzopyran as a white crystalline solid.

NMR (CDCl$_3$): δ 6.3-6.6 (m; 3H); 5.43 (s; 1H); 4.00 (brt(5 Hz); 2H); 2.69 (brt(6 Hz); 2H); 1.7-2.0 (m; 2H).

Step D: Preparation of 7-cinnamyl-2,3-dihydro-6-hydroxybenzopyran

Sodium hydride (0.56 g; 14 mM; 60% in mineral oil) was washed twice with hexane under a stream of nitrogen. It was suspended in 20 ml of anhydrous benzene under a positive pressure of nitrogen and the 2,3-dihydro-6-hydroxybenzopyran (1.40 g; 9.3 mM) was added rapidly dropwise in 30 ml of benzene. This suspension was stirred for one hour at room temperature and then a solution of cinnamyl bromide (2.06 g: 10.5 mM) in 15 ml of benzene was added dropwise. After stirring for 2 hours at ambient temperature the reaction mixture was poured into 1N aqueous hydrochloric acid and partitioned. The aqueous layer was extracted once with ether and the combined organic layers were dried over magnesium sulfate, filtered through a fritted funnel, and stripped of solvent in vacuo. The resulting oil was purified by chromatography twice on the Waters' Prep 500 equipped with one cartridge and eluted first with 15% ethyl acetate in hexane and then with 8% ethyl acetate in hexane with recycling. This produced the two possible cinnamyl alkylated regioisomers, the less polar oil (400 mgs) showed two ortho protons on the benzopyran ring in the NMR. The major product, 7-cinnamyl-2,3-dihydro-6-hydroxybenzopyran, was isolated in 20% (500 mg) and crystallized to a yellow solid.

(a) The 5-cinnamylisomer:

NMR: (DMSO-D$_6$) δ 8.67 (s; 1H); 7.0–7.4 (m; 5H); 6.55 (d(9 Hz); 1H); 6.39 (d(9 Hz); 1H); 6.26 (s; 2H); 3.92 (brt(6 Hz); 2H); 3.33 (brd(8 Hz); 2H); 2.65 (d(t(6 Hz); 2H); 1.6–2.0 (m; 2H).

IR: 3700, 3450, 3000, 2900, 1600, 1475, 1250, 1170, 1090, 1070, 970, 910 cm$^{-1}$ (CHCl$_3$).

MS: 266 (M+, 66%); 162 (100%); 91 (53%).

| Microanalysis: | C | H |
|---|---|---|
| Calculated: | 81.17 | 6.81 |
| Found: | 80.14 | 7.01 |

(b) The 7-cinnamylisomer

NMR: (CDCl$_3$) δ7.0–7.3 (m; 5H); 6.1–6.5 (m; 4H); 4.59 (brs; 1H); 4.02 (brt(5 Hz); 2H); 3.39 (d(4 Hz); 2H); 2.22 (brt(6 Hz); 2H); 1.8–2.1 (m; 2H). (CHCl$_3$) IR: 3800, 3600, 3000, 2900, 1600, 1490, 1420, 1330, 1250, 1150, 1100, 1060, 980, 965, 943, 889 cm$^{-1}$.

MS: 266 (M+, 66%); 162 (100%); 91 (43%).

| Microanalysis: | C | H |
|---|---|---|
| Calculated: | 81.17 | 6.81 |
| Found: | 80.67 | 6.87 | m.p.=99°–101°.

EXAMPLE 6

7-(o-bromocinnamyl)-2,3-dihydro-6-hydroxybenzopyran

Sodium hydride (1.36 g; 34 mM; 60% in mineral oil) was washed twice with hexane under a stream of nitrogen. It was suspended in 50 ml of anhydrous benzene in a 3-necked 500 ml flask equipped with a dropping funnel. To this suspension benzene (75 ml) containing 6-hydroxy dihydrobenzopyran (3.4 g; 22.7 mM) was added. The resulting reaction mixture was stirred at room temperature for about 40 minutes and an additional 30 ml of benzene containing o-bromocinnamyl bromide (7.28 g; 28.4 mM) was added dropwise. This reaction was heated to reflux for 1.5 hours and cooled to ambient temperature. The suspension was poured into 150 ml of cold aqueous 1N hydrochloric acid, partitioned, and the aqueous layers was extracted once with ether. The combined organic phases were dried over magnesium sulfate and stripped of solvent. The resulting oil was chromatographed twice on the Waters Prep 500 equipped with one cartridge. The first elution with 15% ethyl acetate in hexane removed most of the impurities and the mixture of regioisomers obtained was separated by eluting again with 15% ethyl acetate in hexane with three recycles on one column. The less polar component (1.0 g; tan solid) was 5-(o-bromocinnamyl)isomer and the most polar component (1.04 g; recrystallized from ethyl acetate/hexane) was 7-(o-bromocinnamyl)-2-3-dihydro-6-hydroxybenzopyran.

(a) 5-(o-bromocinnamyl)-isomer

NMR (CDCl$_3$): δ6.7–7.5 (m; 4H); 7.11 (d(15 Hz); 1H); 6.53 (s; 1H); 6.40 (s; 1H); 6.15 (d of t (15 Hz and 6 Hz); 1H); 4.67 (brs; 1H); 4.04 (t(5 Hz); 2H); 3.43 (d(6 Hz); 2H); 2.63 (t(7 Hz); 2H); 1.90 (m; 2H).

(b) 7-(o-bromocinnamyl)-isomer

NMR (CDCl$_3$): δ6.8–7.4 (m; 4H); 6.50 (brs; 3H); 6.05 (d of t (15 Hz and 6 Hz); 1H); 4.60 (s; 1H); 4.03 (brt; 2H); 3.46 (d(6 Hz); 2H); 2.73 (brt; 2H); 1.8–2.1 (m; 2H).

EXAMPLE 7

2-(m-Methoxycinnamyl)-4-methoxyphenol

Step A: Preparation of methyl m-methoxycinnamate

Anhydrous methanol (400 ml) was chilled to 0° and treated with acetyl chloride (20 ml) to give a 3% solution of methanolic HCl. m-Methoxycinnamic acid (14.24 g; 80 mM) was added to this solution in one portion and stirred until dissolution was obtained. The reaction mixture was then allowed to stand at ambient temperature overnight. The solvent was removed in vacuo at 35° and the resulting oil was filtered through a one inch pad of silica gel in a 150 ml fritted funnel with 400 ml of a 35% solution of ethyl acetate in hexane. The solvent was then removed in vacuo leaving 14.5 grams of methyl m-methoxycinnamate as an oil.

NMR (CDCl$_3$): δ 7.63 (d(16 Hz); 1H); 6.7–7.3 (m; 4H); 6.36 (d(16 Hz); 1H); 3.77 (s; 6H).

Step B: Preparation of m-methoxy-cinnamyl alcohol

The methyl m-methoxycinnamate was taken up in 50 ml of anhydrous toluene and chilled to −70° under nitrogen. Diisobutylaluminum hydride (54 ml; 83 mM; 1.54M in toluene) was added dropwise through a sidearm addition funnel. Some starting material remained as detected by TLC (35% ethyl acetate/hexane on silica gel) so a further 15 ml of diisobutylaluminum hydride was added. The reaction was allowed to warm to room temperature and then carefully quenched with water at 0° giving an emulsion. The emulsion was taken up in cold 2N aqueous hydrochloric acid and partitioned. The aqueous layer was extracted twice with ether and the combined organic layers were washed with 2.5N aqueous sodium hydroxide and with brine. The organic extracts were then dried over K$_2$CO$_3$ and stripped of volatiles in vacuo. The clear oil was chromatographed on one cartridge in a Water's Prep 500 with 35% ethyl acetate in hexane to give 9.38 g (71% yield) of m-methoxycinnamyl alcohol.

NMR (CDCl$_3$): δ6–7.4 (m; 6H); 4.28 (d(4 Hz); 2H); 3.70 (s; 3H); 1.90 (br; 1H).

Step C: Preparation of m-methoxycinnamylbromide

Pyridinium hydrobromide perbromide (5.00 g; 12.5 mM; 80%) was suspended in 25 ml of chloroform under nitrogen and hexamethyldisilane was added in one portion giving rise to a slightly exothermic reaction. The suspension was chilled to 0° and m-methoxycinnamyl alcohol (1.64 g; 10.0 mM) was slowly added dropwise in 4 ml of chloroform. The reaction was stirred for an additional 30 minutes at 0° and then poured into 50 ml of anhydrous ether. This suspension was washed three times with water and dried over magnesium sulfate. Removal of the solvent under vacuum gave a white solid which was taken up in hexane and filtered through a fritted funnel. The white solid (1.56 g) proved to be simple bromine addition across the double bond. Removal of the hexane from the filtrate gave an oil (1.2 g; 53%) which NMR indicated to be the desired m-methoxycinnamyl bromide. NMR (CDCl$_3$); δ 6.6–7.6 (m; 4H); 6.1–6.6 (m; 2H); 4.30 (d, 6 Hz; 2H); 3.75 (s, 3H).

Step D: Preparation of 2-(m-methoxycinnamyl)-4-methoxyphenol

Sodium hydride (0.40 g; 10.0 mM; 60% in mineral oil) was washed twice with hexane under a stream of nitrogen. The hydride was then suspended in 8 ml of anhydrous benzene and p-methoxyphenol (0.62 g; 5.0 mM) was added in one portion. After stirring at room temperature for fifteen minutes benzene (8 ml) was added containing m-methoxycinnamyl bromide (5.3 mM). The reaction was heated to reflux overnight under an air condenser and quenched by pouring into 1N aqueous hydrochloric acid. This was extracted with ether, dried over magnesium sulfate and stripped in vacuo. In an attempt to remove the starting p-methoxyphenol the resulting brown oil was taken up in ethyl acetate/hexane and washed eight times with water. Drying and solvent removal was followed by flash chromatography on a 30 mm×7½" column of silica gel eluted with 700 ml of 20% ethyl acetate in hexane. This produced a yellow oil (400 mg; 30%) identified by NMR as 2-(m-methoxycinnamyl)-4-methoxyphenol.

IR: 3400, 3000 2880, 1620, 1600, 1510, 1450, 1250, 1050, 990, 880, 790, 700 cm$^{-1}$.

EXAMPLE 8

2-(o-Bromocinnamyl)-4-methoxyphenol

Step A: Preparation of ethyl o-bromocinnamate

Carboethoxymethylidene triphenylphosphorane (94 g, 270 mM) was dissolved in 350 ml of methylenechloride under nitrogen. o-Bromobenzaldehyde (31.5 ml; 270 mM) was added via an addition funnel in 125 ml of methylene chloride. The solution was allowed to stand at room temperature overnight and then the solvent was removed in vacuo. The slushy residue was taken up in 10% ethyl acetate in hexane and filtered through a one-inch pad of silica gel in a 350 ml fritted funnel with one liter of 10% ethyl acetate in hexane. Solvent removal on the rotary evaporator followed by pumping overnight gave 66.3 g of an oil, ethyl o-bromocinnamate in 96% yield. The NMR indicates a 4.5 to 1 mixture of trans to cis isomers. NMR:

trans: 7.95 (d (16 Hz); 1H); 7.0–7.7 (m, 4H); 6.3 (d (16 Hz); 1H); 4.15 (q 6 Hz); 2H); 1.34 (t (7 Hz); 3H).

cis: 5.987 (d (12 Hz)).

Step B: Preparation of 2-(o-bromocinnamyl)-4-methoxyphenol

Sodium hydride (1.68 g; 42 mM; 60% in mineral oil) was washed twice with hexane under a stream of nitrogen. It was then suspended in 75 ml of benzene and another 75 ml of benzene containing p-methoxyphenol (4.45 g; 36 mM) was added dropwise at room temperature. The suspension was stirred for an additional 45 minutes and then 30 ml of benzene containing o-bromocinnamyl bromide (38 mM) was added dropwise. The reaction was heated to 50° under nitrogen for two hours and then cooled to ambient temperature. The quench was accomplished by pouring the reaction into cold dilute hydrochloric acid. The layers were separated and the aqueous phase was extracted once with benzene. The combined organic layers were extracted ten times with water in an effort to remove the p-methoxyphenol and were then dried over magnesium sulfate and stripped of solvent. The resulting oil was purified by chromatography on a Waters Prep 500 equipped with two cartridges and eluted with 20% ethyl acetate in hexane. The 2-(o-bromocinnamyl)-4-methoxyphenol (8.25 g) was isolated as a pale yellow oil in 68% yield.

NMR (CDCl$_3$): δ6.6–7.6 (m; 8H); 6.2 (d of t (16 Hz and 6 Hz); 1H); 4.70 (s; 1H); 3.73 (s; 3H); 3.55 (br d (6 Hz); 2H).

IR: 3500, 1500, 1430, 1200, 1030, 965 cm$^{-1}$.

EXAMPLE 9

2-(o-Cyanocinnamyl)-4-methoxyphenol

Cuprous cyanide (1.03 g; 11.5 mM) and 2-(o-bromocinnamyl)-4-methoxyphenol (1.03 g; 3.23 mM) were combined in 12 ml of anhydrous N-methylpyrrolidinone. Nitrogen was bubbled through the resulting suspension for five minutes and it was then heated to 175° under positive nitrogen pressure for 2 hours. The reaction was poured into 50 ml of conc. NH$_4$OH and 50 ml of water. The emulsion was extracted three times with ether and the ether extracts were washed once with water. Drying over magnesium sulfate was followed by solvent removal leaving a brown oil. This crude product was purified by flash chromatography with 35% ethyl acetate in hexane on a 30 mm×6" column of silica gel. Recrystallization from ethyl acetate/hexane gave 2-(o-cyanocinnamyl)-4-methoxyphenol as a tan solid (335 mg, 39% yield) m.p. 72°–74°.

NMR (CDCl$_3$): δ6.4–7.6 (m; 9H); 3.7 (s; 3H); 3.57 (d (5 Hz); 2H).

IR: 3620, 3350, 2975, 2870, 2250, 1600, 1500, 1440, 1180, 975 cm$^{-1}$.

MS: 265 (M+) (100); 149 (36); 136 (48).

| Micro analysis: | C | H | N |
|---|---|---|---|
| Calc'd. | 76.96 | 5.70 | 5.28 |
| Found: | 76.69 | 5.70 | 5.37 |

EXAMPLE 10

2-(o-Formylcinnamyl)-4-methoxyphenol

A flame-dried flask was charged with 2-(o-cyanocinnamyl)-4-methoxyphenol (1.86 g; 7.0 mM) and 50 ml of anhydrous benzene under nitrogen. The solution was cooled to 0° and a toluene solution of diisobutylaluminum hydride (10.5 ml; 16 mM; 1.53M) was added dropwise via an addition funnel. After 2 hours at 0° a further 5 ml of diisobutylaluminum hydride was added. A small aliquot was worked up at this time and the IR showed the loss of the nitrile absorption of 2250 cm$^{-1}$ and the appearance of a carbonyl stretch at 1700 cm$^{-1}$. The reaction was poured into cold dilute hydrochloric acid solution and partitioned. The organic phase was washed with water and dried over magnesium sulfate. Solvent removal in vacuo left a brown oil which was chromatographed on the Waters Prep 500 equipped with two cartridges and eluted with 35% ethyl acetate in hexane. This gave 0.50 g (27%) of 2-(o-formylcinnamyl)-4-methoxyphenol as an oil.

NMR (CDCl$_3$): δ10.23 (s; 1H); 7.0–7.8 (m; 6H); 6.6–6.9 (m; 3H); 6.20 (d of t (15 Hz and 6 Hz); 1H); 5.4–5.6 (br s; 1H); 3.73 (s; 3H); 3.55 (d (6 Hz); 2H).

IR: cm$^{-1}$ 3350, 2900, 2800, 2700, 1740, 1580, 1480, 1412, 1190, 1020, 950, 790, 730.

EXAMPLE 11

2-(o-Hydroxymethylcinnamyl)-4-methoxyphenol

Sodium borohydride (35 mg) was added in one portion to a solution of 2-(o-formylcinnamyl)-4-methoxyphenol (240 mg; 0.89 mM) in 5 ml of methanol. The reaction was stirred at room temperature for 2 hours and then the solution was removed in vacuo. The residue was taken up in 2N aqueous hydrochloric acid and extracted with ether. The ethereal phase was washed with water, dried over magnesium sulfate, stripped of solvent, and filtered through 1½" of silica gel in a 30 ml fritted funnel with 100 ml of 50% ethyl acetate/hexane providing 240 mg (99%) of pure 2-(o-hydroxymethylcinnamyl)-4-methoxyphenol.

NMR (CDCl$_3$): 7.0–7.4 (m; 4H); 6.4–6.8 (m; 4H); 6.10 (d of t (15 Hz and 6 Hz); 1H); 4.60 (s; 2H); 3.67 (s; 3H); 3.45 (d (6 Hz); 2H).

IR: 3400, 1400, 1230, 1050, 980, 770 (Nujol).

MS: 270 (M+, 6%); 252 (32%); 137 (100%); 136 (30%); 116 (30%).

| Micro analysis: | C | H |
|---|---|---|
| Calc'd. | 75.53 | 6.71 |
| Found: | 74.77 | 6.78 | m.p. = 101°–102°.

EXAMPLE 12

2-(p-Fluorocinnamyl)-4-methoxyphenol

Sodium hydride (0.94 g; 23.5 mM; 60% in mineral oil) was washed twice with hexane under nitrogen in a flame-dried, three-necked, round-bottomed flask. The sodium hydride was then suspended in 35 ml of benzene and 35 ml more of benzene containing p-methoxyphenol (2.48 g; 20 mM) were added. After stirring for 45 minutes at room temperature, p-fluorocinnamyl bromide (4.3 g; 20 mM) was added dropwise in 30 ml of benzene. The reaction mixture was heated to reflux for 20 minutes and then poured into cold 1N aqueous hydrochloric acid. The layers were separated an the aqueous layer was extracted once with benzene. The combined benzene layers were washed five times with water, dried over magnesium sulfate and stripped of solvent leaving a brown residue. This oil was crystallized twice from hexane producing 2.21 g (43%) of tan crystals of 2-(p-fluorocinnamyl)-4-methoxyphenol.

NMR (CDCl$_3$): δ5.9–7.3 (m; 9H); 4.52 (s; 1H); 3.70 (s; 3H); 3.45 (d (6 Hz); 2H).

IR: 3570, 3500, 3420, 2880, 2805, 1590, 1415, 1140, 1080, 1020, 960 cm$^{-1}$.

MS: 258 (M+) (59%); 149 (31%); 136 (100%); 109 (54%); 108 (38%).

| Micro analysis: | C | H | F |
|---|---|---|---|
| Calc'd. | 74.40 | 5.85 | 7.36 |
| Found: | 74.51 | 5.93 | 7.39 | m.p. = 79°–81°.

EXAMPLE 13

2-(o-Fluorocinnamyl)-4-methoxyphenol

Sodium hydride (1.88 g, 47 mM; 60% in mineral oil) was washed twice with hexane under a stream of nitrogen and then suspended in 75 ml of benzene in a flame-dried flask. To this suspension was added 75 ml of anhydrous benzene containing p-methoxyphenol (4.96 g; 40 mM). The deprotection reaction was stirred at room temperature for one hour at which time 30 ml of benzene containing o-fluorocinnamyl bromide (8.60 g; 40 mM) was added. No reaction occurred at room temperature so the mixture was heated to reflux for ten minutes. The suspension was then cooled, poured into 1N aqueous hydrochloric acid and partitioned. The aqueous layer was extracted once with benzene and the combined organic layers were washed five times with water. After drying over magnesium sulfate the solvent was removed and the residue was chromatographed on a Waters Prep 500 equipped with two cartridges and eluted with 20% ethyl acetate in hexane. This produced a brown oil which was seen to be analytically pure 2-(o-fluorocinnamyl)-4-methoxyphenol in 64% yield (6.56 g).

NMR (CDCl$_3$): δ6.15–7.40 (m; 9H); 4.6–4.8 (br s; 1H); 3.66 (s; 3H); 3.47 (d (6 Hz); 2H).

IR: 3350, 3000, 2900, 2800, 1600, 1480, 1440, 1240, 1210, 1185, 1080, 1020, 960, 780, 740 cm$^{-1}$.

MS: 258 (M+) (94%); 149 (48%); 136 (100%); 121 (28%); 109 (53%).

| Micro analysis: | C | H | F |
|---|---|---|---|
| Calc'd. | 74.40 | 5.85 | 7.36 |
| Found: | 74.08 | 5.85 | 7.50 |

EXAMPLE 14

2-Ethoxycarbonyl-1-methyl-4-(2-hydroxy-5-methoxyphenyl)propenylpyrrole

Step A: Preparation of 2-Ethenyl-4-methoxy-1-O-methoxymethylphenol

To a suspension of 104 g (0.291 moles) of methyltriphenylphosphonium bromide in 100 ml dry tetrahydrofuran at 0° was added 115 ml (0.275 moles) of 2.4M n-butyllithium and the dark red solution was stirred at 0° for 30 minutes. Then a solution of 38.2 g (0.195 moles) of 2-(3-oxapropyloxy)-5-methoxybenzaldehyde in 100 ml of dry tetrahydrofuran was added and the solution was stirred at room temperature for 60 minutes. The solution was concentrated and the residue partitioned between ether and water. The ether layer was washed with aqueous Na$_2$CO$_3$, then brine, then dried (Na$_2$SO$_4$) and concentrated. The oily residue was dissolved in 500 ml of 10% ethylacetate-hexane and cooled at 0° overnight, then filtered. The filtrate was concentrated to give 33.8 g (89%) of 2-ethenyl-4-methoxy-1-O-methoxymethylphenol as a pale yellow liquid. NMR (CDCl$_3$) δ3.45 (s, 3H), 3.71 (s, 3H), 5.10 (s, 2H), 5.20 (d of d, 1H), 5.6 (d of d, 1H), 6.5–7.0 (m, 4H).

Step B: Preparation of 2-(2-Hydroxyethyl)-4-methoxy-1-O-methoxymethylphenol To a solution of 33.8 g (0.174 moles) of 2-ethenyl-4-methoxy-1-O-methoxymethylphenol in 300 ml of dry tetrahydrofuran at 0° was added 120 ml of a 1.0M borane-tetrahydrofuran solution. The solution was stirred at room temperature for 60 minutes, cooled to 0° and 48 ml of 10% NaOH was added dropwise. Then 41 ml of 30% H$_2$O$_2$ was added *with caution* and the mixture was stirred at room temperature for 30 minutes. The solution was partitioned between ether and water and the ether layer was washed with aqueous NaHCO₃ and brine, dried (Na₂SO₄) and evaporated. The oily residue was purified by Prep. 500 HPLC using 40% ethylacetatehexane to afford 27.3 g (73%) of 2-(2-hydroxyethyl)-4-methoxy-1-O-methoxymethylphenol as a colorless liquid. NMR (CDCl₃) δ2.15 (s, br, 1H, —OH), 2.8 (t, 2H, J=7 Hz), 3.40 (s, 3H), 3.65 (s, 3H), 3.73 (m, 2H), 5.05 (s, 2H), 6.55 (d of d, 1H), 6.61 (s, 1H), 6.88 (d, 1H).

Step C: Preparation of 2-(2-Iodoethyl)-4-methoxy-1-O-methoxymethylphenol

A solution of 27.3 g (0.129 moles) of 2-(2-hydroxyethyl)-4-methoxy-1-O-methoxymethylphenol, 16 ml pyridine and 15.5 ml (22.9 g, 0.200 moles) in 200 ml of dichloromethane was stirred at 0° for 60 minutes. The solution was partitioned between dichloromethane and water and the organic layer was washed with aqueous NaHCO₃ and brine and then dried (Na₂SO₄) and evaporated.

The residue was dissolved in 300 ml of acetone and to this was added a solution of 96 g (0.640 moles) of NaI in 600 ml acetone. The solution was heated at 60° for 3 hours under N₂, then concentrated, partitioned between ether and water. The ether layer was washed with aqueous Na₂S₂O₇, then brine, dried (Na₂SO₄) and evaporated. The oily residue was chromatographed on a Prep. 500 HPLC using 5% ethyl acetate-hexane to afford 38.1 g (92%) of 2-(2-iodoethyl)-4-methoxy-1-O-methoxymethylphenol as a colorless liquid. NMR (CDCl₃) δ3.25 (m, 4H), 3.50 (s, 3H), 3.75 (s, 3H), 5.10 (s, 2H), 6.6–6.7 (m, 2H), 6.95 (d, 1H).

Step D: Preparation of 2-[2-(3-oxapropyloxy)-5-methoxyphenyl]ethyltriphenyl phosphonium iodide A mixture of 38.1 g (0.118 moles) of 2-(2-iodoethyl)-4-methoxy-1-O-methoxymethylphenol and 38.1 g (0.145 moles) of triphenylphosphine was heated neat at 160° C. After 60 minutes the solution was cooled and the glassy residue was crystallized from CH₂Cl₂-toluene to afford 47.3 g (69%) of 2-[2-(3-oxapropyloxy)-5-methoxyphenyl]ethyltriphenyl phosphonium iodide as a white powder. NMR (CDCl₃) δ3.0 (m, 2H), 3.40 (s, 3H), 3.75 (m, 5H), 5.05 (s, 2H), 6.60 (d of d, 1H, J=7.5, J=2), 6.90 (d, 1H, J=7) 6.98 (d, 1H, J=2), 7.70 (s, 15H).

Step E: Preparation of 2-Ethoxycarbonyl-1-methyl-4-[2-(3-oxapropyloxy)-5-methoxyphenyl]propenylpyrrole A solution of 1.6M n-butyllithium (4.0 ml, 6.0 mmol) was added to a suspension of 3.45 g (5.90 mmol) of 2-[2-(3-oxapropyloxy)-5-methoxyphenyl]ethyltriphenylphosphonium iodide in 20 ml of dry tetrahydrofuran at 0°. After 30 minutes a solution of 1.10 g (6.07 mmol) of 2-ethoxycarbonyl-1-methylpyrrole-2-carboxaldehyde in 5 ml of dry tetrahydrofuran was added and the solution was stirred for 30 minutes. The mixture was partitioned between ether and water and the ether layer was washed with water, dried (Na₂SO₄) and evaporated. The residue was chromatographed on silica using 20% ethylacetatehexane to afford 1.78 g (85%) of 2-ethoxycarbonyl-1-methyl-4-[2-(3-oxapropyloxy)-5-methoxyphenyl]propenylpyrrole as a colorless glass. NMR (CDCl₃) δ1.30 (t, 3H, J=6 Hz), 3.40 (s, 3H), 3.45 (trans), 3.70 (cis) (d, J=6 Hz, total 2H, cis:trans, 1:10), 3.78 (s, 3H), 3.90 (s, 3H), 4.25 (q, 2H, J=6 Hz), 5.0 (trans), 5.05 (cis) (s, total 2H), 5.75–6.6 (m, 2H), 6.7–7.3 (m, 5H).

Step F: Preparation of 2-Ethoxycarbonyl-1-methyl-4-(2-hydroxy-5-methoxyphenyl)propenylpyrrole A solution of 1.00 g (2.79 mmol) of 2-ethoxycarbonyl-1-methyl-4-[2-(3-oxapropyloxy)-5-methoxyphenyl]propenylpyrrole in 5 ml of 1:1 aqueous trifluoroacetic acid was stirred at 0° for 1 hour, then at room temperature for 1 hour. The solution was partitioned between ether and water and the ether layer was washed with 3 portions of water. The ether extract was dried (Na₂SO₄), concentrated, and chromatographed on silica using 20% ethylacetatehexane to afford 0.68 g (77%) 2-ethoxycarbonyl-1-methyl-4-(2-hydroxy-5-methoxyphenyl)propenylpyrrole of a colorless glass. NMR (CDCl₃) δ1.30 (t, 3H, J=6 Hz), 3.4 (trans), 3.65 (cis) (d, total 2H, J=6 Hz, trans:cis=10:1), 3.78 (s, 3H), 3.90 (s, 3H), 4.25 (q, 2H, J=6 Hz), 5.75–6.6 (m, 2H), 6.7–7.3 (m, 5H).

EXAMPLE 15

2-Ethoxycarbonyl-(1-methyl-5-[2-(3-oxapropyloxy)-5-methoxyphenyl]propenylpyrrole

Step A: Preparation of 2-Ethoxycarbonyl-1-methyl-5-[2-(3-oxapropyloxy)-5-methoxyphenyl]propenylpyrrole From 1.1 g (6.07 mmol) 2-ethoxycarbonyl-1-methylpyrrole-5-carboxaldehyde, there was prepared according to the procedures described in Step E of Example 14 1.47 g (69%) of 2-ethoxycarbonyl-1-methyl-5-[2-(3-oxapropyloxy)-5-methoxyphenyl]propenylpyrrole as a colorless glass. NMR (CDCl₃) δ1.30 (t, 3H, J=6 Hz), 3.40 (s, 3H), 3.45 (trans), 3.70 (cis) (d, 2H, J=6 Hz, trans:cis=8:1), 3.80 (s, 3H), 4.20 (s, 3H), 4.30 (q, 2H, J=6 Hz), 5.1 (trans), 5.15 (cis) (s, 2H), 5.8–6.6 (m, 2H), 6.7–7.1 (m, 5).

Step B: Preparation of 2-Ethoxycarbonyl-1-methyl-5-(2-hydroxy-5-methoxyphenyl)propenylpyrrole From 1.0 g of 2-ethoxycarbonyl-1-methyl-5-[2-(3-oxapropyloxy)-5-methoxyphenyl]propenylpyrrole, there was prepared, by the procedures described in Step F of Example 14, 0.74 g (84%) of 2-ethoxycarbonyl-1-methyl-5-(2-hydroxy-5-methoxyphenyl)propenylpyrrole as a colorless glass. NMR (CDCl₃) δ1.30 (t, 3H, J=6 Hz), 3.45 (trans), 3.70 (cis) (d, J=6 Hz, 2H), trans:cis=8:1, 3.80 (s, 3H), 4.20 (s, 3H), 4.30 (q, 2H, J=Hz), 5.8–6.6 (m, 2H), 6.7–7.1 (m, 5H).

EXAMPLE 16

2-(3,4-dimethoxycinnamyl)-4-methoxyphenol

Step A: Preparation of 2-(3,4-dimethoxycinnamyl)-4-methoxy-1-O-methoxymethylphenol From 1.00 g (6.02 mmol) of 3,4-dimethoxybenzaldehyde there was prepared as in Step E of Example 14, 1.63 g (80%) of 2-(3,4-dimethoxycinnamyl)-4-methoxy-1-O-methoxymethylphenol as a colorless glass. NMR (CDCl₃) δ3.43 (s, 3H), 3.46 (trans), 3.68 (cis) (d, 2H, J=7 Hz, trans:cis=3:1), 3.78 (s, 3H), 3.88 (s, 6H), 5.10 (trans), 5.15 (cis) (s, 2H), 5.75–6.5 (m, 2H), 6.6–7.1 (m, 6H).

Step B: Preparation of 2-(3,4-dimethoxycinnamyl)-4-methoxyphenol

Prepared from 1.00 g (2.90 mmol) 2-(3,4-dimethoxycinnamyl)-4-methoxy-1-O-methoxymethylphenol as in Step F of Example 14 to afford 0.66 g (76%) of 2-(3,4-dimethoxycinnamyl)-4-methoxyphenol as a colorless glass. NMR (CDCl$_3$) δ3.45 (trans), 3.66 (cis) (d, 2H, J=7 Hz, trans:cis=3:1) 3.78 (s, 3H), 3.88 (s, 6H), 5.7–6.6 (m, 2H), 6.65–7.0 (m, 6H).

EXAMPLE 17
2-(p-methylthiocinnamyl)-4-methoxyphenol

Step A: Preparation of 2-(p-Methylthiocinnamyl)-4-methoxy-1-methoxymethylphenol From 0.920 g (6.10 mmol) of p-methylthiobenzaldehyde there was prepared as in Step E of Example 14 1.68 g (86%) of 2-(p-methylthiocinnamyl)-4-methoxy-1-methoxymethylphenol as a colorless glass. NMR (CDCl$_3$) δ2.40 (s, 3H), 3.40 (m, 5H), 3.70, s (3H), 5.0 (cis), 5.05 (trans) (s, 2H, trans:cis=4:1) 5.75–6.4 (m, 2H), 6.6–7.2 (m, 5H).

Step B: Preparation of 2-(p-Methylthiocinnamyl)-4-methoxyphenol

From 1.00 g (3.02 mmol) of 2-(p-methylthiocinnamyl) 4-methoxy-1-methoxymethylphenol there was prepared as in Step F of Example 14 0.72 g (83%) of 2-(p-methylthiocinnamyl)-4-methoxyphenol as a colorless glass. NMR (CDCl$_3$) 2.40 (s, 3H), 3.40 (trans), 3.55 (cis) (d, 2H, J=7 Hz, trans:cis=4:1), 3.70 (s, 3H), 5.7–6.4 (m, 2H), 6.6–7.2 (m, 5H).

What is claimed is:

1. A compound of formula (II)

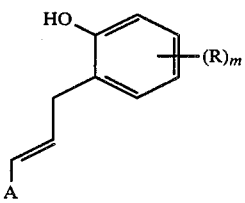

or a pharmaceutically acceptable salt thereof wherein
R is
- (a) COOR$^2$ wherein R$^2$ is H or C$_{1-6}$alkyl;
- (b) loweralkoxy;
- (c) halo C$_{1-6}$alkylcarbonyl;
- (d) halo;
- (e) lowerhaloalkyl;
- (f) hydroxyloweralkyl; or
- (g) cyano;

m is 1 or 2;

A is unsubstituted or substituted heteroaryl selected from a group consisting of:
- (1) thienyl;
- (2) benzothienyl;
- (3) furyl;
- (4) benzofuryl;
- (5) pyrryl;
- (6) pyridyl;
- (7) tetrazolyl; or
- (8) imidazolyl;

the heteroaryl above being substituted with one or two of R$^1$ wherein R$^1$ is
- (1) hydrogen;
- (2) halo;
- (3) loweralkoxy;
- (4) lower alkylthio;
- (5) lower alkyl sulfinyl;
- (6) lower alkyl sulfonyl;
- (7) loweralkyl;
- (8) lower alkanoyl;
- (9) haloloweralkyl;
- (10) —COOH;
- (11) —COOC$_2$H$_5$;
- (12) hydroxyloweralkyl;
- (13) halo loweralkanoyl or
- (14) loweralkanoyloxy.

2. The compound of claim 1 wherein
R is loweralkoxy;
m is 1; and
A is unsubstituted or substituted heteroaryl selected from a group consisting of
- (1) thienyl;
- (2) benzothienyl;
- (3) imidazolyl; or
- (4) pyrryl.

3. The compound of claim 1 wherein
R is methoxy;
m is 1; and
A is
(a)

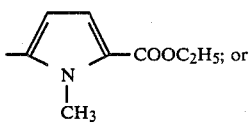

(b)

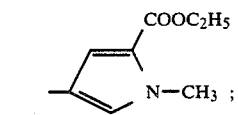

4. A method of treating or decreasing topical inflammation comprising the administration to a mammalian species in need of such treatment of a therapeutically effective amount of a compound of formula (II)

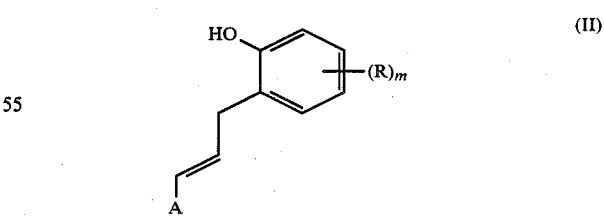

or a pharmaceutically acceptable salt thereof wherein
R is
- (a) COOR$^2$ wherein R$^2$ is H or C$_{1-6}$alkyl;
- (b) loweralkoxy;
- (c) halo C$_{1-6}$alkylcarbonyl;
- (d) halo;
- (e) lowerhaloalkyl;
- (f) hydroxyloweralkyl; or (g) cyano;

m is 1 or 2;

A is unsubstituted or substituted heteroaryl selected from a group consisting of:
(1) thienyl;
(2) benzothienyl;
(3) furyl;
(4) benzofuryl;
(5) pyrryl;
(6) pyridyl;
(7) tetrazolyl; or
(8) imidazolyl;

the heteroaryl above being substituted with one or two of $R^1$ wherein $R^1$ is
(1) hydrogen;
(2) halo;
(3) loweralkoxy;
(4) lower alkylthio;
(5) lower alkyl sulfinyl;
(6) lower alkyl sulfonyl;
(7) loweralkyl;
(8) lower alkanoyl;
(9) haloloweralkyl;
(10) —COOH;
(11) —COOC$_2$H$_5$;
(12) hydroxyloweralkyl;
(13) halo loweralkanoyl; or
(14) loweralkanoyloxy.

5. The method of treatment of claim 4 wherein

R is loweralkoxy;

m is 1; and

A is unsubstituted or substituted heteroaryl selected from a group consisting of
(1) thienyl;
(2) benzothienyl;
(3) imidazolyl; or
(4) pyrryl.

6. The method of treatment of claim 4 wherein

R is methoxy;

m is 1; and

A is (a)

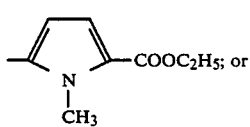

(b)

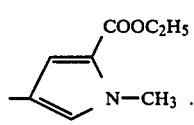

7. A pharmaceutical composition for treating topical inflammation comprising a pharmaceutical carrier and an effective amount of a compound of formula (II)

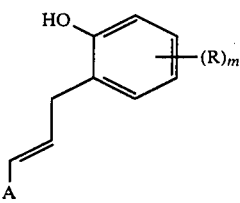

or a pharmaceutically acceptable salt thereof wherein R is
(a) COOR$^2$ wherein R$^2$ is H or C$_{1-6}$alkyl;
(b) loweralkoxy;
(c) halo C$_{1-6}$alkylcarbonyl;
(d) halo;
(e) lowerhaloalkyl;
(f) hydroxyloweralkyl; or
(g) cyano;

m is 1 or 2;

A is unsubstituted or substituted heteroaryl selected from a group consisting of:
(1) thienyl;
(2) benzothienyl;
(3) furyl;
(4) benzofuryl;
(5) pyrryl;
(6) pyridyl;
(7) tetrazolyl; or
(8) imidazolyl;

the heteroaryl above being substituted with one or two of $R^1$ wherein $R^1$ is
(1) hydrogen;
(2) halo;
(3) loweralkoxy;
(4) lower alkylthio;
(5) lower alkyl sulfinyl;
(6) lower alkyl sulfonyl;
(7) loweralkyl;
(8) lower alkanoyl;
(9) haloloweralkyl;
(10) —COOH;
(11) —COOC$_2$H$_5$;
(12) hydroxyloweralkyl;
(13) halo loweralkanoyl; or
(14) loweralkanoyloxy.

8. The composition of claim 7 wherein

R is loweralkoxy;

m is 1; and

A is unsubstituted or substituted heteroaryl selected from a group consisting of
(1) thienyl;
(2) benzothienyl;
(3) imidazolyl; or
(4) pyrryl.

9. The composition of claim 7 wherein

R is methoxy;

m is 1; and

A is (a)

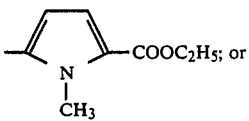

(b)

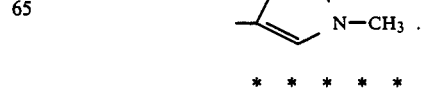

* * * * *